United States Patent
Chang et al.

(10) Patent No.: US 10,519,317 B2
(45) Date of Patent: Dec. 31, 2019

(54) GOLD PIGMENT WITH HIGH COLOR STRENGTH

(71) Applicant: CQV CO., LTD., Jincheon-gun, Chungcheongbuk-do (KR)

(72) Inventors: Kil-Wan Chang, Cheongju-si (KR); Kwang-Soo Lim, Jincheon-gun (KR); Byung-Ki Choi, Cheongju-si (KR); Jin-Hyoung Lee, Cheongju-si (KR)

(73) Assignee: CQV CO., LTD., Jincheon-Gun, Chungcheongbuk-Do (KR)

( * ) Notice: Subject to any disclaimer, the term of this patent is extended or adjusted under 35 U.S.C. 154(b) by 0 days.

(21) Appl. No.: 15/576,299

(22) PCT Filed: Jun. 2, 2016

(86) PCT No.: PCT/KR2016/005824
§ 371 (c)(1),
(2) Date: Nov. 22, 2017

(87) PCT Pub. No.: WO2016/200091
PCT Pub. Date: Dec. 15, 2016

(65) Prior Publication Data
US 2018/0148576 A1 May 31, 2018

(30) Foreign Application Priority Data
Jun. 10, 2015 (KR) .......................... 10-2015-0082060

(51) Int. Cl.
| | | |
|---|---|---|
| *C09C 1/00* | (2006.01) | |
| *C09D 7/62* | (2018.01) | |
| *A61K 8/19* | (2006.01) | |
| *A61K 8/25* | (2006.01) | |
| *A61K 8/29* | (2006.01) | |
| *C08K 3/22* | (2006.01) | |
| *C08K 3/34* | (2006.01) | |
| *C08K 9/02* | (2006.01) | |
| *A61K 8/02* | (2006.01) | |
| *A61Q 1/04* | (2006.01) | |
| *C09D 167/00* | (2006.01) | |

(52) U.S. Cl.
CPC ............ *C09C 1/0024* (2013.01); *A61K 8/022* (2013.01); *A61K 8/0233* (2013.01); *A61K 8/19* (2013.01); *A61K 8/25* (2013.01); *A61K 8/29* (2013.01); *A61Q 1/04* (2013.01); *C08K 3/22* (2013.01); *C08K 3/34* (2013.01); *C08K 9/02* (2013.01); *C09D 7/62* (2018.01); *C09D 167/00* (2013.01); *A61K 2800/43* (2013.01); C08K 2003/2241 (2013.01); C08K 2003/2262 (2013.01); C08K 2003/2272 (2013.01); C09C 2200/102 (2013.01); C09C 2220/106 (2013.01)

(58) Field of Classification Search
None
See application file for complete search history.

(56) References Cited

U.S. PATENT DOCUMENTS

| | | | | |
|---|---|---|---|---|
| 4,192,691 | A | * | 3/1980 | Armanini .............. C09C 1/0015 106/417 |
| 5,776,845 | A | * | 7/1998 | Boulos ..................... C03C 3/078 501/64 |
| 6,599,355 | B1 | | 7/2003 | Schmidt et al. |
| 2005/0142084 | A1 | * | 6/2005 | Ganguly .................. A61K 8/26 424/63 |
| 2008/0305184 | A1 | * | 12/2008 | Heinz ..................... C09D 7/69 424/646 |
| 2012/0301554 | A1 | | 11/2012 | Kniess |
| 2013/0108569 | A1 | | 5/2013 | Hochstein et al. |
| 2018/0148576 | A1 | * | 5/2018 | Chang ...................... C09C 3/06 |

FOREIGN PATENT DOCUMENTS

| | | |
|---|---|---|
| CN | 101460572 A | 6/2009 |
| CN | 102167916 A | 8/2011 |
| JP | 2585128 B2 | 2/1997 |
| JP | 2003-183538 A | 7/2003 |
| JP | 2010-500402 A | 1/2010 |
| JP | 4558283 B2 | 10/2010 |
| JP | 2011-174067 A | 9/2011 |
| JP | 2014-077137 A | 5/2014 |
| KR | 1997-0001474 A | 1/1997 |
| KR | 2002-0070428 A | 9/2002 |

OTHER PUBLICATIONS

Malvern Instruments. Sample Dispersion and Refractive Index Guide. (Year: 2007).*
European Search Report dated Jul. 4, 2018, issued in corresponding European Patent Application No. 16807732.9.
International Search Report dated Oct. 17, 2016 corresponding to International Application No. PCT/KR2016/005824.

(Continued)

*Primary Examiner* — Katherine Peebles
(74) *Attorney, Agent, or Firm* — Hauptman Ham, LLP

(57) ABSTRACT

A gold pigment is disclosed. The gold pigment according to the present disclosure includes a substrate; a first coating layer formed on a surface of the substrate and including a metal oxide having a refractive index of more than 1.8; a second coating layer formed on the first coating layer and including an oxide containing manganese; a third coating layer formed on the second coating layer and including a colorless metal oxide having a refractive index of 1.8 or less; a fourth coating layer formed on the third coating layer and including a metal oxide having a refractive index of more than 1.8; and a fifth coating layer formed on the fourth coating layer and including $Fe_2O_3$.

10 Claims, 2 Drawing Sheets

(56) References Cited

OTHER PUBLICATIONS

Japanese Office Action dated Oct. 19, 2018, in connection with the Japanese Patent Application No. 2018-514762.
Chinese Office Action dated Jun. 25, 2019 for corresponding Chinese Application No. 201680030337.4.

* cited by examiner

| Fe₂O₃ | ←350 |
| TiO₂ | ←340 |
| SiO₂ | ←330 |
| MnO | ←320 |
| TiO₂ | ←310 |
| Substrate | ←100 |

| Comparative Example 1 | Example 1 |

US 10,519,317 B2

GOLD PIGMENT WITH HIGH COLOR STRENGTH

CROSS REFERENCE TO RELATED APPLICATION

This present application is a national stage filing under 35 U.S.C § 371 of PCT application number PCT/KR2016/005824 filed on Jun. 2, 2016 which is based upon and claims the benefit of priority to Korean Patent Application No. 10-2015-0082060 filed on Jun. 10, 2015, in the Korean Intellectual Property Office. The disclosures of the above-listed applications are hereby incorporated by reference herein in their entirety.

TECHNICAL FIELD

The present disclosure relates to a gold pigment, and more particularly to a novel gold pigment in which reddish tone is lessened by controlling the lamination structure of coating layers and laminated materials thereof, thereby improving gold aesthetic.

BACKGROUND ART

Gold pigments are gold-colored pigments and are used for aesthetic effects in various fields. For example, it has been used in industrial applications such as wallpaper, laminate, plastic molding, leather coating, silk printing, offset printing, painting of household appliances, and ceramic applications. For cosmetics, it is also used in various color cosmetics such as lipstick, nail polish, hair gel, eye shadow, and lip gloss. In addition, gold pigments are used in automotive interior and exterior paintings, construction and ship paints where high weatherability is required.

Korean Laid-open Patent Publication No. 1997-0001474 (Publication Date: Jan. 24, 1997) (hereinafter referred to as Patent Document 1) discloses a gold pigment.

Patent Document 1 discloses a gold pigment which can be used in paints, varnishes, powder coatings, printing inks, plastics and cosmetic formulations, wherein titanium dioxide ($TiO_2$) and iron oxide ($Fe_2O_3$) are sequentially coated on a substrate.

However, only limited gold color can be obtained with white titanium dioxide and red iron oxide alone, and therefore it is difficult to properly realize gold color which has lesser red tones required by consumers.

Further, Korean Laid-open Patent Publication No. 2002-0070428 (Publication Date: Sep. 9, 2002) (hereinafter referred to as Patent Document 2) discloses a gold pigment.

FIG. 1 shows a conventional gold pigment, and schematically shows a gold pigment that can be derived from Patent Document 2.

Referring to FIG. 1, the illustrated gold pigment includes, on a substrate 100, a first layer 110 formed by mixing $TiO_2$ and $Fe_2O_3$, a second layer 120 formed of $SiO_2$, a third layer 130 formed of $TiO_2$, and a fourth layer 140 formed of $Fe_2O_3$ or a mixture of $Fe_2O_3$ and $TiO_2$.

FIG. 2 schematically shows another conventional gold pigment.

Referring to FIG. 2, the illustrated gold pigment includes, on a substrate 100, a first layer 210 formed of $TiO_2$, a second layer 220 formed of $SiO_2$, a third layer 230 formed of $TiO_2$, and a fourth layer 240 formed of $Fe_2O_3$, similarly to the gold pigment shown in FIG. 1.

In the case of the gold pigment shown in FIGS. 1 and 2, there is a limitation that gold color is obtained by a combination of white titanium dioxide and red iron oxide in general, except that a coating layer formed of colorless $SiO_2$ is formed in an intermediate layer.

DISCLOSURE

Technical Problem

It is an aspect of the present disclosure to provide a novel gold pigment which is less reddish and can represent gold colors more accurately.

Technical Solution

In accordance with one aspect of the present disclosure, a gold pigment includes a plurality of layered structure having a coating layer containing $TiO_2$ and a coating layer containing $Fe_2O_3$, on a substrate, wherein the coating layer containing $Fe_2O_3$ is located on an upper side of the coating layer containing $TiO_2$ and a coating layer containing an oxide containing manganese is formed between the coating layer containing $Fe_2O_3$ and the coating layer containing $TiO_2$.

In accordance with another aspect of the present disclosure, a gold pigment includes a substrate; a first coating layer formed on a surface of the substrate and including a metal oxide having a refractive index of more than 1.8; a second coating layer formed on the first coating layer and including an oxide containing manganese; a third coating layer formed on the second coating layer and including a colorless metal oxide having a refractive index of 1.8 or less; a fourth coating layer formed on the third coating layer and including a metal oxide having a refractive index of more than 1.8; and a fifth coating layer formed on the fourth coating layer and including $Fe_2O_3$.

Preferably, the first coating layer is formed of only $TiO_2$.

The second coating layer may include at least one of MnO and $MnO_2$.

The third coating layer may include at least one of $SiO_2$, $MgO.SiO_2$, and $Al_2O_3$.

The fourth coating layer may include $TiO_2$.

Preferably, the thickness of the second coating layer is the smallest among the first to fifth coating layers.

Advantageous Effects

The gold pigment according to the present disclosure can additionally include a manganese-containing oxide coating layer such as a blackish brown MnO in addition to a $TiO_2$ coating layer and an $Fe_2O_3$ coating layer, thereby obtaining a gold color with less red tones.

In addition, the gold pigment according to the present disclosure is less reddish, has excellent gloss, and has a strong sparkling impact.

BEST MODE

Advantages and features of the present disclosure, and methods of achieving the same will be apparent with reference to the embodiments described below in detail. However, the present disclosure is not limited to the embodiments described below, but may be embodied in various forms. It is to be understood that the embodiments of the present disclosure are for the completeness of the disclosure and are provided to fully disclose the scope thereof to a person having ordinary skill in the art to which the present disclosure belongs. The present disclosure is only defined by the scope of the accompanying claims.

Hereinafter, a gold pigment according to the present disclosure will be described in detail with reference to the accompanying drawings.

Figure 3:
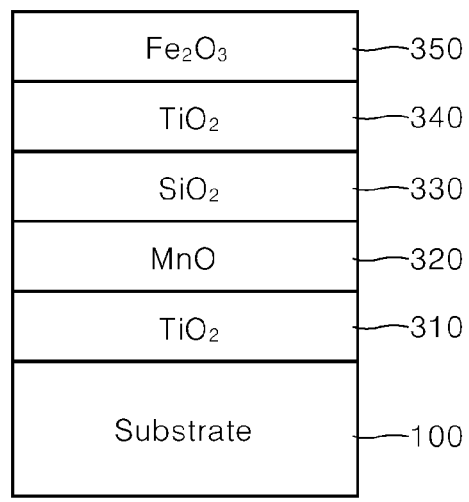
FIG. 3 schematically shows a gold pigment according to one embodiment of the present disclosure.

FIG. 3 schematically shows a gold pigment according to one embodiment of the present disclosure.

Referring to FIG. 3, a gold pigment according to an embodiment of the present disclosure includes a substrate 100, a first coating layer 310, a second coating layer 320, a third coating layer 330, a fourth coating layer 340, and a fifth coating layer 350.

The coating layers 310 to 350 are each formed to a thickness of about 0.5 μm or less and may be formed at 60° C. to 90° C., respectively.

The first to fifth coating layers 310 to 350 may be formed only once in this order, and may be formed repeatedly in this order more than once, if necessary. In addition, an additional coating layer may be further formed between each coating layer, and a protective coating layer may be further formed on the fifth coating layer 350, that is, the uppermost coating layer, for the purpose of improving weatherability or the like.

The substrate 300 may be formed of natural mica, synthetic mica, glass flake, alumina flake, or the like. The substrate 300 may generally be a platelet substrate having a particle size of about 5 to 600 μm, but is not limited thereto and various known substrates can be used.

The first coating layer 310 is formed on the surface of the substrate 300 and includes a metal oxide having a refractive index of more than 1.8. The first coating layer 210 is a powder having a gold color under a black background and serves to determine a basic color.

At this time, the first coating layer may be formed to have a thickness of about 100 to 200 nm with only $TiO_2$. $TiO_2$ may have a rutile or an anatase structure, and more preferably a rutile structure. In the case of rutile structure $TiO_2$, there is an advantage that the gloss and the stability are more excellent. Such rutile structure $TiO_2$ coating layer may be formed by pretreating the substrate surface with a tin compound such as $SnCl_4$ and then coating $TiO_2$ with $TiCl_4$ or the like.

When the first coating layer 310 and the fourth coating layer 340 described later are formed of $TiO_2$, the first coating layer 310 and the fourth coating layer 340 may be formed from $TiCl_4$ under strong acidic conditions of pH 3 or less.

The second coating layer 320 is formed on the first coating layer 310 and includes an oxide containing manganese such as MnO. Such manganese-containing oxides may include MnO and $MnO_2$, and they are blackish brown, and any one of them may be used, or both of them may be used in combination.

The gold color realized by a white $TiO_2$ coating layer and a red $Fe_2O_3$ coating layer is somewhat reddish. However, as in the present disclosure, a Mn-containing oxide coating layer (such as 320 in FIG. 3) such as MnO between the white $TiO_2$ coating layer (such as 310 in FIG. 3) and the red $Fe_2O_3$ (such as 350 in FIG. 3) is included, the gold color can be more accurately represented by removing some of the red tone from the conventional reddish gold color.

The second coating layer 320 comprising a manganese-containing oxide may be formed from $MnCl_2$ under neutral conditions of pH 6 to 8.

The third coating layer 330 is formed on the second coating layer 320 to a thickness of about 10 to 200 nm and includes a colorless metal oxide having a refractive index of 1.8 or less. The third coating layer 230 is a low refractive index layer which is positioned between a high refractive index layer (such as 310 in FIG. 3) and a high refractive index layer (such as 340 and 350 in FIG. 3) to allow for the gold pigment according to the present disclosure to act as an interference pigment.

The colorless metal oxide having a refractive index of 1.8 or less may include at least one of $SiO_2$, $MgO.SiO_2$, and $Al_2O_3$.

The fourth coating layer 340 is formed on the surface of the third coating layer 330 and includes a metal oxide having a refractive index of more than 1.8. The fourth coating layer 340 may be formed of a white metal oxide, for example, $TiO_2$ coating layer.

The fifth coating layer 350 is formed on the fourth coating layer 340 and includes $Fe_2O_3$.

Such $Fe_2O_3$ corresponds to a high refractive red metal oxide having a refractive index exceeding 1.8.

The fifth coating layer may be formed from an iron-containing compound such as $FeCl_3$ or the like under an acidic condition of pH 2 to 4.

A desired effect can be achieved when the thickness of the second coating layer 320 including a manganese oxide is a specific thickness among the first to fifth coating layers 310 to 350. If the thickness of the manganese oxide is too thin, the effect of reducing the red tone may be insufficient, and if it is too thick, the gloss or the like may be deteriorated. More preferably, the content of the second coating layer may be 0.1 to 10 parts by weight based on 100 parts by weight of the substrate, wherein the thickness of the second coating layer may be 0.1 to 20 nm.

The gold pigment of the present disclosure does not have to include all of the five coating layers shown in FIG. 2, and all of the conditions including three or more coating layers as described below are included in the scope of the present disclosure.

That is, the gold pigment of the present disclosure has a plurality of layered structure in which a coating layer containing $TiO_2$ and a coating layer containing $Fe_2O_3$ are formed on the substrate, but any of those structures in which the coating layer containing $Fe_2O_3$ is located on an upper side of the coating layer containing $TiO_2$, and a coating layer containing a manganese-containing oxide is formed between a coating layer containing $Fe_2O_3$ and a coating layer containing $TiO_2$ can be applied to the present disclosure.

EXAMPLES

Hereinafter, the present disclosure will be described in more detail with reference to preferred embodiments thereof. It is to be understood, however, that the embodiments are intended to be illustrative and are not to be construed as limiting the disclosure in any way.

The contents not described herein can be sufficiently technically inferred to those having ordinary skill in the art, and a description thereof will be omitted.

1. Preparation of Gold Pigments

Example 1

100 g of synthetic mica flakes having a particle size of 5 to 560 μm were introduced into 1 L demineralized water and stirred to form a slurry. Then, after the slurry was heated to 75° C., the pH of the slurry was adjusted to 1.7 by adding an HCl solution (Formation of substrate slurry).

Then, 30 g of $SnCl_4$ solution ($SnCl_4$ content 11 wt. %) was weighed and titrated in the slurry at a constant rate over 1 hour while the pH was kept constant at 1.7 with 30% NaOH diluent.

Then, 300 g of $TiCl_4$ solution ($TiCl_4$ content 33 wt. %) was weighed and titrated in the slurry over 8 hours while the pH was kept constant at 1.7 with 30% NaOH diluent. After titration, the mixture was refluxed for 10 minutes, and the pH was adjusted to 7.0 with 20% NaOH diluent (Formation of first coating layer).

Then, 100 g of $MnCl_2$ solution ($MnCl_2$ content 3 wt. %) was weighed and titrated in the slurry over 2 hours while the pH was kept constant at 6.0 to 8.0 with 30% NaOH diluent. After titration, the mixture was refluxed for 10 minutes, and the pH was adjusted to 7.5 with 20% NaOH diluent (Formation of second coating layer).

Then, 900 g of $MgO.SiO_2$ solution ($MgO.SiO_2$ content 3.5 wt. %) was weighed and titrated in the slurry over 4 hours while the pH was kept constant at 7.5 with HCl solution. Then, an HCl solution was added to adjust the pH of the slurry to 1.7, and the mixture was further refluxed with stirring for 15 minutes (Formation of third coating layer).

Then, 30 g of $SnCl_4$ solution ($SnCl_4$ content 11 wt. %) was weighed and titrated in the slurry at a constant rate over 1 hour while the pH was kept constant at 1.7 with 30% NaOH diluent.

Then, 250 g of $TiCl_4$ solution ($TiCl_4$ content 33 wt. %) was weighed and titrated in the slurry over 8 hours while the pH was kept constant with 30% NaOH diluent (Formation of fourth coating layer).

After titration, the mixture was refluxed for 10 minutes, and the pH was adjusted to 3.2 with 20% NaOH diluent.

Then, 150 g of $FeCl_3$ solution ($FeCl_3$ content 20 wt. %) was weighed and titrated in the slurry over 2 hours while the pH was kept constant at 3.2 with 30% NaOH diluent (Formation of fifth coating layer).

After refluxing, the final slurry was filtered off and dewatered, washed twice with demineralized water, and then dried at 120° C. for 10 hours to give an intermediate product in powder form.

Then, the obtained intermediate product was calcined at 800° C. for 12 minutes to obtain a gold pigment powder.

Example 2

100 g of synthetic mica flakes having a particle size of 5 to 560 μm were introduced into 1 L demineralized water and stirred to form a slurry. Then, after the slurry was heated to 75° C., the pH of the slurry was adjusted to 1.7 by adding an HCl solution (Formation of substrate slurry).

Then, 300 g of $TiCl_4$ solution ($TiCl_4$ content 33 wt. %) was weighed and titrated in the slurry over 8 hours while the pH was kept constant at 2.4 with 30% NaOH diluent. After titration, the mixture was refluxed for 10 minutes, and the pH was adjusted to 7.0 with 20% NaOH diluent (Formation of first coating layer).

Then, 100 g of $MnCl_2$ solution ($MnCl_2$ content 3 wt. %) was weighed and titrated in the slurry over 2 hours while the pH was kept constant at 6.0 to 8.0 with 30% NaOH diluent. After titration, the mixture was refluxed for 10 minutes, and the pH was adjusted to 7.5 with 20% NaOH diluent (Formation of second coating layer).

Then, 900 g of $MgO.SiO_2$ solution ($MgO.SiO_2$ content 3.5 wt. %) was weighed and titrated in the slurry over 4 hours while the pH was kept constant at 7.5 with HCl solution. Then, an HCl solution was added to adjust the pH of the slurry to 2.4, and the mixture was further refluxed with stirring for 15 minutes (Formation of third coating layer).

Then, 250 g of $TiCl_4$ solution ($TiCl_4$ content 33 wt. %) was weighed and titrated in the slurry over 8 hours while the pH was kept constant with 30% NaOH diluent (Formation of fourth coating layer).

After titration, the mixture was refluxed for 10 minutes, and the pH was adjusted to 3.2 with 20% NaOH diluent.

Then, 150 g of $FeCl_3$ solution ($FeCl_3$ content 20 wt. %) was weighed and titrated in the slurry over 2 hours while the pH was kept constant at 3.2 with 30% NaOH diluent (Formation of fifth coating layer).

After refluxing, the final slurry was filtered off and dewatered, washed twice with demineralized water, and then dried at 120° C. for 10 hours to give an intermediate product in powder form.

Then, the obtained intermediate product was calcined at 800° C. for 12 minutes to obtain a gold pigment powder.

In the gold pigment powder prepared according to Example 1, the $TiO_2$ structure of the first coating layer and the fourth coating layer showed a rutile structure, whereas in the gold pigment powder prepared according to Example 2, the $TiO_2$ structure of the first coating layer and the fourth coating layer exhibited an anatase structure.

Comparative Example 1

100 g of mica with a particle size of 10 to 60 μm was heated to 75° C. in 2 L demineralized water. When the temperature was reached, a solution of 130.5 g of $FeCl_3 \times 6H_2O$, 46.5 g of $TiCl_4$ and 11.6 g of $AlCl_3 \times 6H_2O$ in 84.3 g of demineralized water was slowly added dropwise with vigorous stirring. The pH was maintained at 2.6 with 32% aqueous solution of sodium hydroxide. After addition of the solution, the mixture was further stirred for approximately 15 minutes. Then, the pH was raised to 7.5 with a 32% aqueous solution of sodium hydroxide, and 431 g of a sodium water glass solution (13.5% of $SiO_2$) was slowly added dropwise at this pH. Then, the mixture was lowered to pH 2.0 with 10% hydrochloric acid, and then the mixture was further stirred for 15 minutes and 396 g of a $TiCl_4$ solution (370 g/L of $TiCl_4$) was added dropwise. The pH was maintained at 2.6 with 32% aqueous solution of sodium hydroxide. After addition of the solution, the mixture was further stirred for approximately 15 minutes. The pH was then raised to 5.0 with 32% solution of sodium hydroxide, and the mixture was stirred for additional 15 minutes.

After refluxing, the final slurry was filtered off and dewatered, washed twice with demineralized water, and then dried at 120° C. for 10 hours to give an intermediate product in powder form.

Then, the obtained intermediate product was calcined at 800° C. for 12 minutes to obtain a gold pigment powder.

Figure 1:
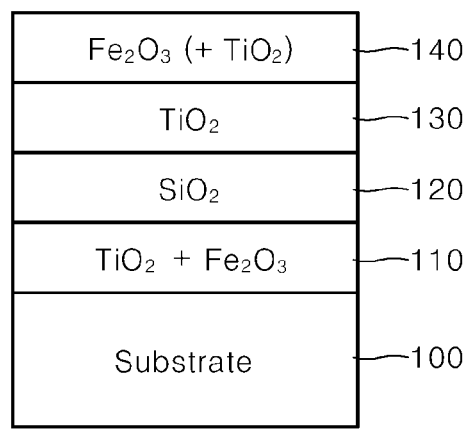
FIG. 1 schematically shows a conventional gold pigment.

The gold pigment powder prepared according to Comparative Example 1 had the structure shown in FIG. 1.

Comparative Example 2

100 g of synthetic mica flakes having a particle size of 5 to 560 μm were introduced into 1 L demineralized water and stirred to form a slurry. Then, after the slurry was heated to 75° C., the pH of the slurry was adjusted to 1.7 by adding an HCl solution (Formation of substrate slurry).

Then, 30 g of SnCl$_4$ solution (SnCl$_4$ content 11 wt. %) was weighed and titrated in the slurry at a constant rate over 1 hour while the pH was kept constant at 1.7 with 30% NaOH diluent.

Then, 300 g of TiCl$_4$ solution (TiCl$_4$ content 33 wt. %) was weighed and titrated in the slurry over 8 hours while the pH was kept constant at 1.7 with 30% NaOH diluent. After titration, the mixture was refluxed for 10 minutes, and the pH was adjusted to 7.5 with 20% NaOH diluent (Formation of first coating layer).

Then, 900 g of MgO.SiO$_2$ solution (MgO.SiO$_2$ content 3.5 wt. %) was weighed and titrated in the slurry over 4 hours while the pH was kept constant at 7.5 with HCl solution. Then, an HCl solution was added to adjust the pH of the slurry to 1.7, and the mixture was further refluxed with stirring for 15 minutes (Formation of second coating layer).

Then, 30 g of SnCl$_4$ solution (SnCl$_4$ content 11 wt. %) was weighed and titrated in the slurry at a constant rate over 1 hour while the pH was kept constant at 1.7 with 30% NaOH diluent.

Then, 250 g of TiCl$_4$ solution (TiCl$_4$ content 33 wt. %) was weighed and titrated in the slurry over 8 hours while the pH was kept constant with 30% NaOH diluent (Formation of third coating layer).

After titration, the mixture was refluxed for 10 minutes, and the pH was adjusted to 3.2 with 20% NaOH diluent.

Then, 150 g of FeCl$_3$ solution (FeCl$_3$ content 20 wt. %) was weighed and titrated in the slurry over 2 hours while the pH was kept constant at 3.2 with 30% NaOH diluent (Formation of fourth coating layer).

After refluxing, the final slurry was filtered off and dewatered, washed twice with demineralized water, and then dried at 120° C. for 10 hours to give an intermediate product in powder form.

Then, the obtained intermediate product was calcined at 800° C. for 12 minutes to obtain a gold pigment powder.

Figure 2:
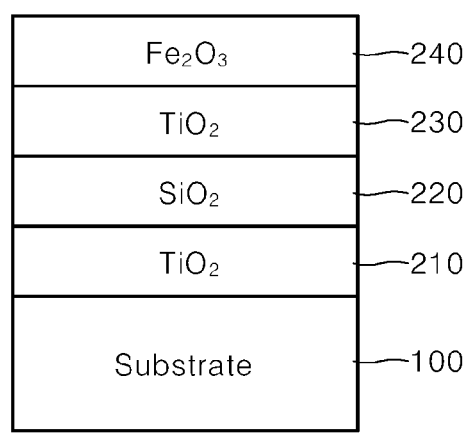
FIG. 2 schematically shows another conventional gold pigment.

The gold pigment powder prepared according to Comparative Example 2 had the structure shown in FIG. 2.

2. Evaluation of Physical Properties

Evaluation of Saturation

Table 1 shows color difference values (a*, b*) of the gold pigments according to Example 1 and Comparative Examples 1 and 2. The color difference value was determined with Konika Minolta Chroma meter CR-400 D65, where L* indicates glossiness, a* is the red coordinate, b* is the yellow coordinate, and ΔL*. Δa* and Δb* are color difference values between the Comparative Example and Example 1 having the same substrates and colors.

Figure 4:
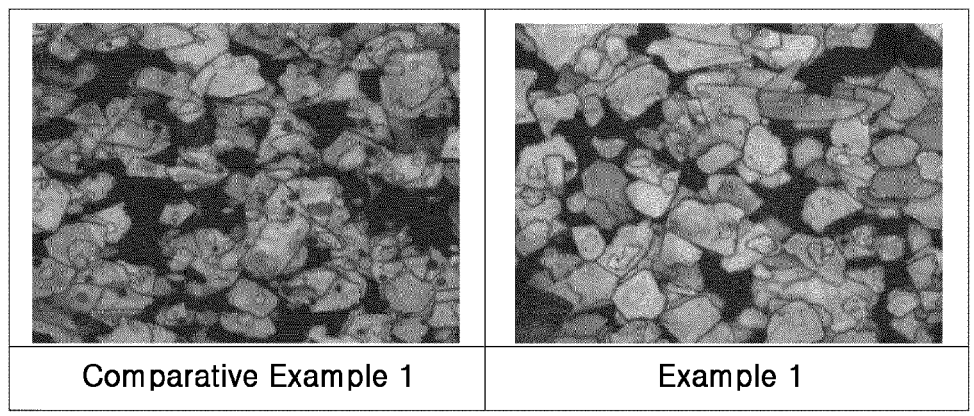
FIG. 4 show optical microscope (×50 magnification) photographs of gold pigments according to Comparative Example 1 and Example 1.

In addition, FIG. 4 shows optical microscope (×50 magnification) photographs of gold pigments according to Comparative Example 1 and Example 1.

TABLE 1

|  | L* | a* | b* | ΔL* | Δa* | Δb* |
| --- | --- | --- | --- | --- | --- | --- |
| C. Ex. 1 | 74.87 | 3.21 | 55.67 | — | — | — |
| C. Ex. 2 | 71.33 | 0.14 | 49.74 | −3.54 | −3.08 | −5.92 |
| Ex. 1 | 78.24 | −0.74 | 57.01 | +3.37 | −3.95 | +1.35 |

Referring to Table 1 and FIG. 4, it can be seen that the color difference values (L*, a*, b*) were changed after the MnO coating layer was used, as a result of comparing Comparative Examples with Example 1.

More specifically, in the case of Example 1, Red color decreased and Yellow color increased as compared with Comparative Examples 1 and 2, and thereby the red tone decreased and the gloss was rather increased

[Applications]

The following is a description of application examples in which the gold pigment obtained in Example 1 is used in paints, plastics, inks and cosmetics.

(1) Paints

This is an example of paints for use in automotive surface coatings.

{Base Coating Composition}

[Polyester Resin]

Hayikyu base for toning transparent (BC-1000) (available from NOROO Painting & Coating Co., Ltd.)

Hayikyu LV thinner (DR-950WS) (available from NOROO Painting & Coating Co., Ltd.)

4 parts by weight of the gold pigment obtained in Example 1 and 96 parts by weight of the polyester resin composition were mixed, and 100 parts by weight of a diluent for the polyester resin was added to the mixture and the viscosity was reduced to a concentration suitable for spray coating (applied using Ford Cup #4 for 14 to 16 seconds (25° C.), which was then applied by spray coating to form an undercoat layer. An uncolored surface clear paint of the following composition was applied over the undercoat layer.

{Surface Clear Paint}

Hayikyu UltraClear (available from NOROO Paintings & Coating Co., Ltd.)

Hayikyu UltraClear hardener (CCH-100) (available from NOROO Painting & Coating Co., Ltd.)

After surface coating, the paint was exposed to air at 40° C. for 30 minutes and heated for curing at 130° C. for 30 minutes.

(2) Plastics

The following are an example of pigment compositions used to color plastics.

Polyethylene resin (pellet): 70 parts by weight

The gold pigment obtained in Example 1: 1 part by weight

Zinc stearate 0.2 part by weight

Liquid paraffin: 0.1 part by weight

The pellets containing the composition were dry blended and extruded.

(3) Cosmetics

The following are compositions for lip-color cosmetics.

Hydrogenated Castor Oil—37 parts by weight

Octyldodecanol—10 parts by weight

Diisostearyl Malate—20 parts by weight

Ceresin—5 parts by weight

*Euphorbia* Cerifera (Candelilla) Wax—5 parts by weight

Dipentaerythrityl Hexahydroxystearate/Hexastearate/Hexarosinate—18.5 parts by weight Copernicia Cerifera (Carnauba) Wax—3 parts by weight Isopropyl Lanolate—1 part by weight VP/Hexadecene Copolymer—1 part by weight The gold pigment obtained in Example 1: Proper amount Antioxidants, preservatives and fragrances: Small amount Lipstick was formed from the composition.

While the present disclosure has been described in connection with what is presently considered to be practical exemplary embodiments, it is to be understood that the disclosure is not limited to the disclosed embodiments, but, on the contrary, the present disclosure may be embodied in other specific forms without departing from the spirit or essential characteristics thereof. It is therefore to be understood that the above-described embodiments are illustrative in all aspects and not restrictive.

The invention claimed is:

1. A gold pigment comprising:
   a substrate;
   a first coating layer formed on the surface of the substrate and comprising a metal oxide having a refractive index of more than 1.8;
   a second coating layer formed on the first coating layer and comprising an oxide containing manganese, wherein the oxide containing manganese is formed from $MnCl_2$ under a condition of pH 6 to 8;
   a third coating layer formed on the second coating layer and comprising a colorless metal oxide having a refractive index of 1.8 or less;
   a fourth coating layer formed on the third coating layer and comprising a metal oxide having a refractive index of more than 1.8; and
   a fifth coating layer formed on the fourth coating layer and containing $Fe_2O_3$.

2. The gold pigment according to claim 1, wherein the first coating layer is formed only of $TiO_2$.

3. The gold pigment according to claim 1, wherein the first coating layer and the fourth coating layer comprise a rutile or anatase $TiO_2$ structure.

4. The gold pigment according to claim 1, wherein the thickness of the second coating layer comprising the oxide containing manganese ranges from 0.1 nm to 20 nm.

5. The gold pigment according to claim 1, wherein the third coating layer comprises at least one selected from the group consisting of $SiO_2$, $MgO.SiO_2$, and $AlO_3$.

6. The gold pigment according to claim 1, wherein the fourth coating layer comprises $TiO_2$.

7. A gold pigment comprising a plurality of layered structure having a coating layer containing $TiO_2$ and a coating layer containing $Fe_2O_3$, on a substrate, wherein
   the coating layer containing $Fe_2O_3$ is located on an upper side of the coating layer containing $TiO_2$,
   a coating layer containing an oxide containing manganese is formed between the coating layer containing $Fe_2O_3$ and the coating layer containing $TiO_2$, and
   the oxide containing manganese is from $MnCl_2$ under a condition of pH 6 to 8.

8. The gold pigment according to claim 1, wherein the thickness of the first coating layer ranges from 100 nm to 200 nm.

9. The gold pigment according to claim 1, wherein the e thickness of the second coating layer is the smallest among the thicknesses of the first coating layer to the fifth coating layer.

10. The gold pigment according to claim 1, wherein the thickness of the third coating layer ranges from 10 nm to 200 nm.

* * * * *